(12) United States Patent
Ishizaki (10) Patent No.: US 11,421,567 B2
(45) Date of Patent: Aug. 23, 2022

(54) CONTROLLER AND CONTROL METHOD FOR VEHICLE

(71) Applicant: TOYOTA JIDOSHA KABUSHIKI KAISHA, Toyota (JP)

(72) Inventor: Noriya Ishizaki, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 17/453,012

(22) Filed: Nov. 1, 2021

(65) Prior Publication Data

US 2022/0145786 A1    May 12, 2022

(30) Foreign Application Priority Data

Nov. 12, 2020   (JP) .............................. JP2020-188467

(51) Int. Cl.
   *F01M 11/10*   (2006.01)
   *G01N 33/28*   (2006.01)

(52) U.S. Cl.
   CPC ......... *F01M 11/10* (2013.01); *F01M 2011/14* (2013.01); *F01M 2011/148* (2013.01); *F01M 2011/1473* (2013.01); *F01M 2250/60* (2013.01); *F02N 2250/02* (2013.01); *G01N 33/2888* (2013.01)

(58) Field of Classification Search
   None
   See application file for complete search history.

(56) References Cited

U.S. PATENT DOCUMENTS

| | | | | | |
|---|---|---|---|---|---|
| 4,109,506 | A | * | 8/1978 | Bassoli | G01B 7/14 73/114.55 |
| 4,417,561 | A | * | 11/1983 | Yasuhara | F01M 11/10 123/196 R |
| 4,497,200 | A | * | 2/1985 | Tournier | G01K 3/04 73/61.76 |
| 4,506,337 | A | * | 3/1985 | Yasuhara | B60R 16/0234 701/29.5 |
| 4,733,556 | A | * | 3/1988 | Meitzler | B01D 27/08 340/631 |
| 4,862,393 | A | * | 8/1989 | Reid | F16N 29/04 701/29.5 |
| 5,060,156 | A | * | 10/1991 | Vajgart | G07C 5/006 701/29.5 |

(Continued)

FOREIGN PATENT DOCUMENTS

| | | |
|---|---|---|
| JP | 2004-257289 A | 9/2004 |
| JP | 2013-075537 A | 4/2013 |
| JP | 2018-096258 A | 6/2018 |

*Primary Examiner* — Kevin R Steckbauer
(74) *Attorney, Agent, or Firm* — Oblon, McClelland, Maier & Neustadt, L.L.P.

(57) ABSTRACT

A controller for a vehicle is configured to execute a lubricating oil degradation degree acquisition process that calculates a degradation degree of a lubricating oil that lubricates an internal combustion engine, a battery degradation degree acquisition process that calculates a degradation degree of a battery, and an oil change time calculation process that calculates an oil change time for the lubricating oil from the degradation degree of the lubricating oil and the degradation degree of the battery. The oil change time calculation process includes calculating the oil change time so as to become earlier as the degradation degree of the battery increases.

8 Claims, 5 Drawing Sheets

(56) References Cited

U.S. PATENT DOCUMENTS

| | | | | |
|---|---|---|---|---|
| 5,530,647 A * | 6/1996 | Sem | ............... | F01M 11/10 701/29.5 |
| 5,633,796 A * | 5/1997 | Cullen | ............... | F16N 29/04 701/29.5 |
| 6,037,864 A * | 3/2000 | Sem | ............... | B60R 16/0234 340/679 |
| 6,509,749 B1 * | 1/2003 | Buelna | ............... | F01M 11/10 324/698 |
| 6,917,865 B2 * | 7/2005 | Arai | ............... | F01M 11/10 701/29.5 |
| 7,835,875 B2 * | 11/2010 | Halalay | ............... | G01N 33/2888 702/50 |
| 7,928,741 B2 * | 4/2011 | Hedges | ............... | G01N 33/2888 324/698 |
| 8,087,287 B2 * | 1/2012 | Cummings | ............... | G01N 33/2876 436/60 |
| 9,244,054 B2 * | 1/2016 | Schneider | ............... | G16Z 99/00 |
| 9,341,129 B2 * | 5/2016 | Leone | ............... | F01M 11/10 |
| 9,415,762 B2 * | 8/2016 | Treharne | ............... | F02N 11/0829 |
| 9,523,320 B2 * | 12/2016 | Leone | ............... | F02D 41/2451 |
| 10,254,270 B2 * | 4/2019 | Potyrailo | ............... | G01N 33/2888 |
| 10,260,388 B2 * | 4/2019 | Potyrailo | ............... | G01N 33/2888 |
| 10,329,973 B2 * | 6/2019 | Handa | ............... | F01M 11/10 |
| 10,427,668 B2 * | 10/2019 | Martin | ............... | F01M 1/16 |
| 10,466,152 B2 * | 11/2019 | Gillette, II | ............... | G01N 11/00 |
| 2004/0093150 A1 * | 5/2004 | Arai | ............... | F01M 11/10 701/104 |
| 2006/0042966 A1 * | 3/2006 | Hariu | ............... | G01N 33/2888 205/787.5 |
| 2007/0194801 A1 * | 8/2007 | Hedges | ............... | G01N 33/2888 324/698 |
| 2009/0201036 A1 * | 8/2009 | Hedges | ............... | G01N 33/2888 324/698 |
| 2010/0116022 A1 * | 5/2010 | Cummings | ............... | G01N 33/2876 73/61.41 |
| 2010/0250156 A1 * | 9/2010 | Halalay | ............... | F01M 11/10 702/50 |
| 2010/0300781 A1 * | 12/2010 | Leone | ............... | B60W 20/40 180/65.265 |
| 2011/0267080 A1 * | 11/2011 | Hedges | ............... | G01N 33/2888 324/698 |
| 2013/0268182 A1 * | 10/2013 | Treharne | ............... | F02N 11/0829 903/905 |
| 2014/0019068 A1 * | 1/2014 | Schneider | ............... | G01N 33/2888 702/30 |
| 2014/0058647 A1 * | 2/2014 | Haladyna | ............... | B60W 10/06 701/104 |
| 2015/0105995 A1 * | 4/2015 | Leone | ............... | F02D 41/04 701/102 |
| 2015/0105996 A1 * | 4/2015 | Leone | ............... | F02D 41/04 701/103 |
| 2017/0081997 A1 * | 3/2017 | Potyrailo | ............... | G01N 33/2888 |
| 2017/0102308 A1 * | 4/2017 | Gillette, II | ............... | F01M 11/10 |
| 2017/0138922 A1 * | 5/2017 | Potyrailo | ............... | G01M 13/021 |
| 2017/0276039 A1 * | 9/2017 | Handa | ............... | F01M 11/10 |
| 2017/0284068 A1 * | 10/2017 | Nakamura | ............... | G01N 33/30 |
| 2018/0299355 A1 * | 10/2018 | Young | ............... | G06N 20/10 |
| 2020/0056971 A1 * | 2/2020 | Gillette, II | ............... | F01M 11/10 |

* cited by examiner

CONTROLLER AND CONTROL METHOD FOR VEHICLE

BACKGROUND

1. Field

The present disclosure relates to a controller and a control method for a vehicle.

2. Description of Related Art

Japanese Laid-Open Patent Publication No. 2018-096258 discloses a vehicle that includes an internal combustion engine and a controller for the internal combustion engine. The controller calculates the degradation degree of a lubricating oil from, for example, the torque of the internal combustion engine and the travel distance of the vehicle, which is equipped with the internal combustion engine. Further, the controller calculates the oil change time for the lubricating oil in correspondence with the degradation degree of the lubricating oil.

In the vehicle, as the degradation degree of a lubricating oil in the internal combustion engine increases, the amount of load needed to start the internal combustion engine increases. The technique disclosed in the above-described document calculates the oil change time for a lubricating oil in correspondence with the degradation degree of the lubricating oil. Thus, when a user changes the lubricating oil at the oil change time, situations in which the internal combustion engine is unable to be started are avoided to a certain extent. However, even if the lubricating oil has not degraded much, the internal combustion engine may be unable to be started depending on the state of the vehicle. The technique disclosed in the above-described document only refers to the degradation degree of a lubricating oil when calculating the oil change time for the lubricating oil. Accordingly, the internal combustion engine is potentially unable to be started at a time before the oil change time for the lubricating oil.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

An aspect of the present disclosure provides a controller for a vehicle. The vehicle includes an internal combustion engine, a motor that starts the internal combustion engine, and a battery that supplies power to the motor. The controller is configured to execute a lubricating oil degradation degree acquisition process that calculates a degradation degree of a lubricating oil that lubricates the internal combustion engine, a battery degradation degree acquisition process that calculates a degradation degree of the battery, and an oil change time calculation process that calculates an oil change time for the lubricating oil from the degradation degree of the lubricating oil and the degradation degree of the battery. The oil change time calculation process includes calculating the oil change time so as to become earlier as the degradation degree of the battery increases.

In the configuration, as the degradation degree of the battery increases, the load amount that can be output from the motor decreases. Thus, at a large degradation degree of the battery, the internal combustion engine is potentially unable to be started by the motor even if the degradation degree of the lubricating oil is not large. In the configuration, the oil change time is calculated so as to become earlier as the degradation degree of the battery increases. Accordingly, even if the load amount that can be output from the motor is decreased by an increase in the degradation degree of the battery, situations in which the internal combustion engine is unable to be started are avoided by changing the lubricating oil.

The controller for the vehicle may be configured to execute an ambient temperature acquisition process that obtains a predicted temperature outside the vehicle when the internal combustion engine is started next. The controller may execute the oil change time calculation process when the predicted temperature is lower than a preset specific temperature.

In the configuration, the controller executes the oil change time calculation process when the predicted temperature is smaller than the specific temperature, that is, when the influence of the battery degradation is large. This prevents the oil change time calculation process from being executed unnecessarily when the degradation of the battery demonstrates a relatively small influence and the internal combustion engine can be started.

In the controller for the vehicle, the vehicle may include an ambient temperature sensor that measures a temperature outside the vehicle. The ambient temperature acquisition process may include obtaining the predicted temperature by estimating the predicted temperature from changes in an ambient temperature over a fixed period obtained from the ambient temperature sensor.

The configuration allows the predicted temperature to be obtained from changes in the ambient temperature over the fixed period obtained from the ambient temperature sensor. This allows the predicted temperature to be obtained without, for example, communicating with a device outside the vehicle.

In the controller for the vehicle, the vehicle may include a communication device capable of communicating with a device outside the vehicle. The controller may be configured to execute a data acquisition process that obtains, through the communication device, ambient temperature data related to a future temperature outside the vehicle. The ambient temperature acquisition process may include obtaining the predicted temperature by estimating the predicted temperature from the ambient temperature data obtained by the data acquisition process.

The configuration allows the predicted temperature to be obtained from the ambient temperature data, which is obtained through the communication device. This allows the predicted temperature to be obtained without, for example, using the ambient temperature sensor in the vehicle.

The controller for the vehicle may further include a memory device that stores multiple periods into which a specific fixed period is divided and stores a temperature corresponding to each of the multiple periods. The controller may be configured to execute a date-and-time acquisition process that obtains date and time when the internal combustion engine is started. The ambient temperature acquisition process may include obtaining the predicted temperature by estimating, as the predicted temperature, a temperature corresponding to one of the periods that includes the date and time.

In the configuration, even if the value of the temperature outside the vehicle is not directly obtained, the predicted temperature can be obtained from the temperature information that includes the date and time.

The controller for the vehicle may be configured to execute an ambient temperature acquisition process that obtains a predicted temperature outside the vehicle when the internal combustion engine is started next. The ambient temperature acquisition process may include obtaining, as the predicted temperature, a temperature outside the vehicle at the next start time obtained by the next start estimation process.

The configuration increases the likelihood of improving the accuracy of the predicted temperature.

The controller for the vehicle may be configured to execute an ambient temperature acquisition process that obtains a predicted temperature outside the vehicle when the internal combustion engine is started next. The oil change time calculation process may include calculating the oil change time so as to become earlier as the predicted temperature decreases as compared with when the predicted temperature increases.

In the configuration, in a case where the degradation degree of the battery increases, the load amount that can be output from the motor tends to decrease as the temperature of the battery decreases. The configuration corrects the oil change time so as to become earlier as the predicted temperature obtained by the ambient temperature obtaining process decreases. This allows the oil change time to be adjusted in correspondence with the predicted temperature.

Another aspect of the present disclosure provides a method for controlling a vehicle. The vehicle includes an internal combustion engine, a motor that starts the internal combustion engine, and a battery that supplies power to the motor. The method includes calculating a degradation degree of a lubricating oil that lubricates the internal combustion engine, calculating a degradation degree of the battery, and calculating an oil change time for the lubricating oil from the degradation degree of the lubricating oil and the degradation degree of the battery. The calculating the oil change time includes calculating the oil change time so as to become earlier as the degradation degree of the battery increases.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

This description provides a comprehensive understanding of the methods, apparatuses, and/or systems described. Modifications and equivalents of the methods, apparatuses, and/or systems described are apparent to one of ordinary skill in the art. Sequences of operations are exemplary, and may be changed as apparent to one of ordinary skill in the art, with the exception of operations necessarily occurring in a certain order. Descriptions of functions and constructions that are well known to one of ordinary skill in the art may be omitted.

Exemplary embodiments may have different forms, and are not limited to the examples described. However, the examples described are thorough and complete, and convey the full scope of the disclosure to one of ordinary skill in the art.

In this specification, "at least one of A and B" should be understood to mean "only A, only B, or both A and B."

First Embodiment

Schematic Configuration of Vehicle

A first embodiment of the present invention will now be described. First, the schematic configuration of a vehicle VC equipped with a controller 100 of the present disclosure will be described.

Figure 1:
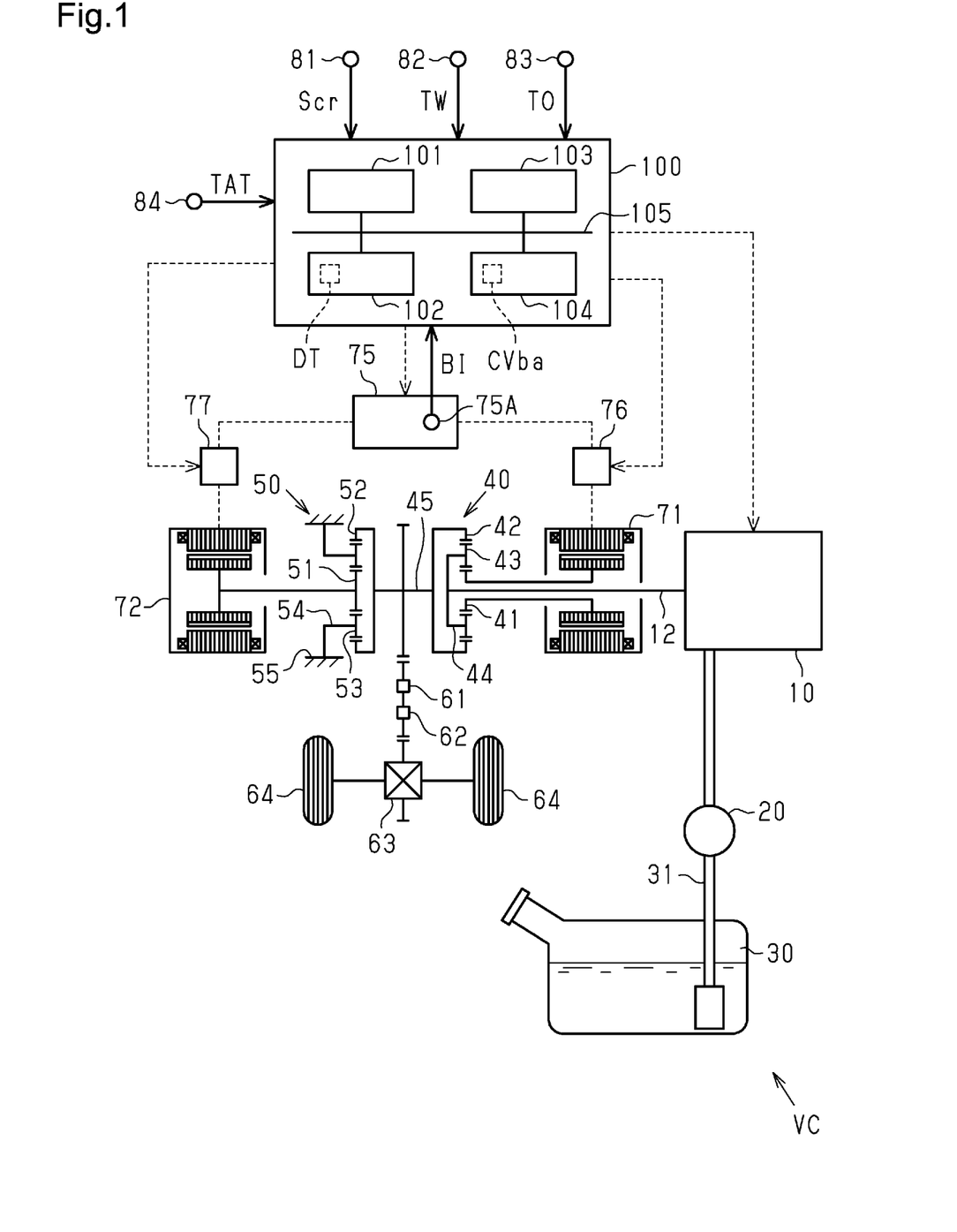
FIG. 1 is a diagram schematically showing the configuration of a vehicle according to a first embodiment.

As shown in FIG. 1, the vehicle VC includes an internal combustion engine 10, a first motor generator 71, and a second motor generator 72 that serve as drive sources. The first motor generator 71 and the second motor generator 72 each has the functionality of an electric motor and a generator. Thus, the vehicle VC is a hybrid electric vehicle.

The internal combustion engine 10 includes an output shaft 12. The output shaft 12 is connected to the pistons (not shown) of the internal combustion engine 10. The reciprocating motion of the pistons rotates the output shaft 12. That is, the output shaft 12 is rotated by the internal combustion engine 10, which functions as a drive source.

The vehicle VC includes a first planetary gear mechanism 40, a ring gear shaft 45, a second planetary gear mechanism 50, an automatic transmission 61, a speed reduction mechanism 62, a differential mechanism 63, and two drive wheels 64. These components form a transmission path of driving force.

The first planetary gear mechanism 40 includes a sun gear 41, a ring gear 42, pinion gears 43, and a carrier 44. The sun gear 41 is an external gear. The ring gear 42 is an internal gear arranged outward from the sun gear 41. The ring gear 42 is rotatable relative to the sun gear 41 and coaxial with the sun gear 41. The pinion gears 43 are arranged between the sun gear 41 and the ring gear 42. The pinion gears 43 are each meshed with the sun gear 41 and the ring gear 42. The pinion gears 43 are connected to the carrier 44. The carrier 44 supports the pinion gears 43 so that the pinion gears 43 can freely rotate and orbit.

In the first planetary gear mechanism 40, the carrier 44 is connected to the output shaft 12. The sun gear 41 is connected to the first motor generator 71. The ring gear 42 is connected to the ring gear shaft 45.

The ring gear shaft 45 is connected to the automatic transmission 61. The automatic transmission 61 is a multi-gear transmission capable of shifting the gear ratio in stages with planetary gear mechanisms (not shown). The automatic transmission 61 is connected to the right and left drive wheels 64 via the speed reduction mechanism 62 and the differential mechanism 63. The torque received from the automatic transmission 61 is reduced in speed by the speed reduction mechanism 62 at a specific speed reduction ratio and is then output. The differential mechanism 63 allows for a difference in the rotation speeds of the right and left drive wheels 64.

The second planetary gear mechanism 50 includes a sun gear 51, a ring gear 52, pinion gears 53, a carrier 54, and a case 55. The sun gear 51 is an external gear. The ring gear 52 is an internal gear arranged outward from the sun gear 51. The ring gear 52 is rotatable relative to the sun gear 51 and coaxial with the sun gear 51. The pinion gears 53 are arranged between the sun gear 51 and the ring gear 52. The pinion gears 53 are each meshed with the sun gear 51 and the ring gear 52. The pinion gears 53 are connected to the carrier 54. The carrier 54 supports the pinion gears 53 so that the pinion gears 53 freely rotate. The carrier 54 is fixed to the case 55. Accordingly, the carrier 54 supports the pinion gears 53 so that the pinion gears 53 are unable to orbit.

In the second planetary gear mechanism 50, the sun gear 51 is connected to the second motor generator 72. The ring gear 52 is connected to the ring gear shaft 45. Accordingly, the ring gear 52 is connected to the right and left drive wheels 64 via the ring gear shaft 45, the speed reduction mechanism 62, and the differential mechanism 63.

The vehicle VC includes a battery 75, a first inverter 76, and a second inverter 77 that transfer electric power. When the first motor generator 71 and the second motor generator 72 function as generators, the battery 75 stores the power generated by the first motor generator 71 and the second motor generator 72. When the first motor generator 71 and the second motor generator 72 function as electric motors, the battery 75 supplies power to the first motor generator 71 and the second motor generator 72.

The first inverter 76 regulates the amount of power transferred between the first motor generator 71 and the battery 75. The second inverter 77 regulates the amount of power transferred between the second motor generator 72 and the battery 75.

The vehicle VC includes an oil pan 30, an oil passage 31, and an oil pump 20 that form a hydraulic circuit. The oil pan 30 stores a lubricating oil that lubricates the internal combustion engine 10. The oil pan 30 is connected to the internal combustion engine 10 via the oil passage 31. The oil pump 20 is arranged in the oil passage 31. The oil pump 20 draws the lubricating oil from the oil pan 30 and supplies the lubricating oil to the internal combustion engine 10.

The vehicle VC includes a crank angle sensor 81. The crank angle sensor 81 detects a crank angle Scr. The crank angle Scr is a rotation angle of the output shaft 12 of the internal combustion engine 10. The crank angle Scr is an angle at which the output shaft 12 is rotated from a reference position.

The vehicle VC includes a coolant temperature sensor 82. The coolant temperature sensor 82 detects a coolant temperature TW. The coolant temperature TW is the temperature of coolant used to cool the internal combustion engine 10.

The battery 75 includes a battery sensor 75A. The battery sensor 75A detects battery information BI that includes the input current, output current, output voltage, and temperature of the battery 75. Particularly, the battery sensor 75A detects the output voltage at the battery 75 when the internal combustion engine 10 is started by the first motor generator 71. This output voltage is referred to as the dropped peak voltage VS (described later).

The vehicle VC includes an oil temperature sensor 83. The oil temperature sensor 83 is located in the oil pan 30. The oil temperature sensor 83 detects an oil temperature TO. The oil temperature TO is the temperature of a lubricating oil in the oil pan 30. The vehicle VC includes an ambient temperature sensor 84. The ambient temperature sensor 84 detects a temperature TAT outside the vehicle VC.

Controller

The vehicle VC includes the controller 100. The controller 100 receives a signal indicating the crank angle Scr from the crank angle sensor 81. The controller 100 receives a signal indicating the coolant temperature TW from the coolant temperature sensor 82. The controller 100 receives a signal indicating the battery information BI from the battery sensor 75A. The controller 100 receives a signal indicating the oil temperature TO from the oil temperature sensor 83. The controller 100 receives a signal indicating the temperature TAT from the ambient temperature sensor 84.

The controller 100 includes a CPU 101, peripheral circuitry 102, a ROM 103, a memory device 104, and a bus 105. The bus 105 connects the CPU 101, the peripheral circuitry 102, the ROM 103, and the memory device 104 such that they are communicable with each other. The peripheral circuitry 102 includes various circuits such as a circuit that generates a clock signal specifying an internal operation, a power supply circuit, and a reset circuit. The ROM 103 stores, in advance, various programs with which the CPU 101 executes various types of control.

The CPU 101 is configured to control the internal combustion engine 10, the first motor generator 71, the second motor generator 72, and the automatic transmission 61 by executing the various programs stored in the ROM 103. That is, the CPU 101 is an execution device.

Viscosity Acquisition Process

The CPU 101 is configured to execute a viscosity acquisition process that obtains a viscosity VO of a lubricating oil. The ROM 103 stores a viscosity acquisition map that indicates the relationship between the oil temperature TO and the viscosity VO of a lubricating oil. In the viscosity acquisition map, the viscosity VO of a lubricating oil decreases in correspondence with an increase in the oil temperature TO. The viscosity acquisition map is defined by conducting experiments and/or simulations in advance. The CPU 101 is configured to obtain the viscosity VO of the lubricating oil by calculating the viscosity VO of the lubricating oil in reference to the oil temperature TO and the viscosity acquisition map received from the oil temperature sensor 83.

Lubricating Oil Degradation Degree Acquisition Process

Figure 2:
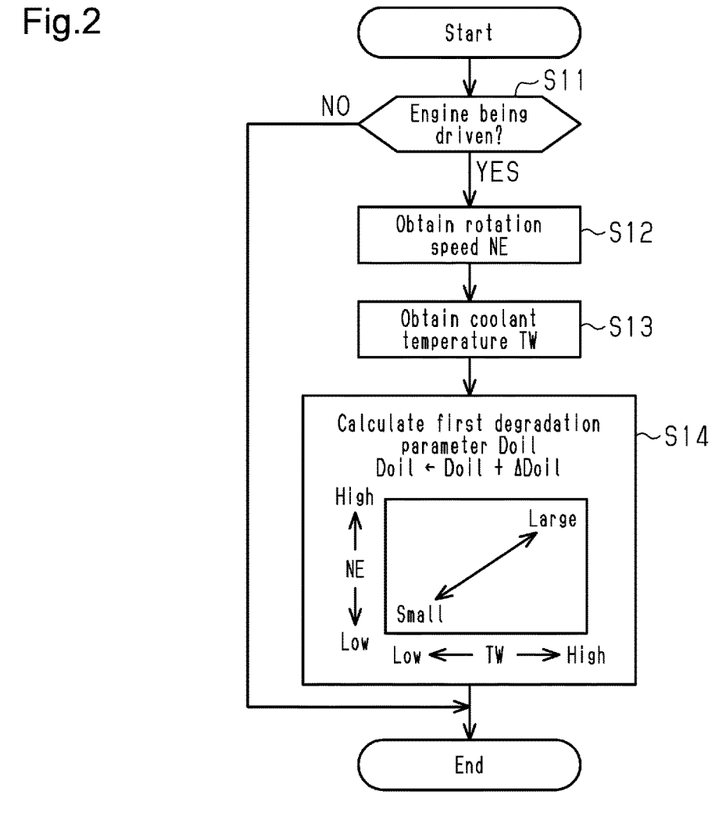
FIG. 2 is a flowchart showing a lubricating oil degradation degree acquisition process in the first embodiment.

The CPU 101 is configured to execute a lubricating oil degradation degree acquisition process that obtains a first degradation parameter Doil. The first degradation parameter Doil is used to quantify the degradation degree of a lubricating oil. The ROM 103 stores a lubricating oil degradation degree acquisition program in advance. The CPU 101 is configured to repeatedly execute the lubricating oil degradation degree acquisition program in, for example, a specific cycle. The value of the first degradation parameter Doil increases as the degradation degree increases.

As shown in FIG. 2, when starting the lubricating oil degradation degree acquisition program, the CPU 101 first executes the process of step S11. In step S11, the CPU 101 determines whether the internal combustion engine 10 is being driven. When determining that the internal combustion engine 10 is not being driven (S11: NO), the CPU 101 ends the series of processes.

When determining that the internal combustion engine 10 is being driven (S11: YES), the CPU 101 advances the process to step S12. In step S12, the CPU 101 obtains a rotation speed NE of the output shaft 12. The CPU 101 obtains the rotation speed NE of the output shaft 12 of the internal combustion engine 10 by calculating the rotation speed NE in reference to the crank angle Scr. Then, the CPU 101 advances the process to step S13.

In step S13, the CPU 101 obtains the coolant temperature TW, which is the temperature of coolant. Then, the CPU 101 advances the process to step S14.

In step S14, the CPU 101 uses a degradation update amount calculation map to calculate a degradation update amount ΔDoil in correspondence with the rotation speed NE and the coolant temperature TW. The CPU 101 updates the first degradation parameter Doil by adding the degradation update amount ΔDoil to the first degradation parameter Doil.

To calculate the degradation update amount ΔDoil, the CPU 101 refers to the degradation update amount calculation map. The memory device 104 stores the degradation update amount calculation map. The degradation update amount calculation map defines the relationship between the degradation update amount ΔDoil and the rotation speed NE and the relationship between the degradation update amount ΔDoil and the coolant temperature TW. In the degradation update amount calculation map, the degradation update amount ΔDoil increases in correspondence with an increase in the rotation speed NE. Further, in the degradation update amount calculation map, the degradation update amount ΔDoil increases in correspondence with an increase in the coolant temperature TW. Then, the CPU 101 temporarily ends the series of processes related to the lubricating oil degradation degree acquisition program. The first degradation parameter Doil is reset when the lubricating oil is changed. For example, when the lubricating oil is changed at a dealership, the resetting simply needs to be performed by inputting to the controller 100 a signal indicating the oil has been changed.

Battery Degradation Degree Acquisition Process

Figure 3:
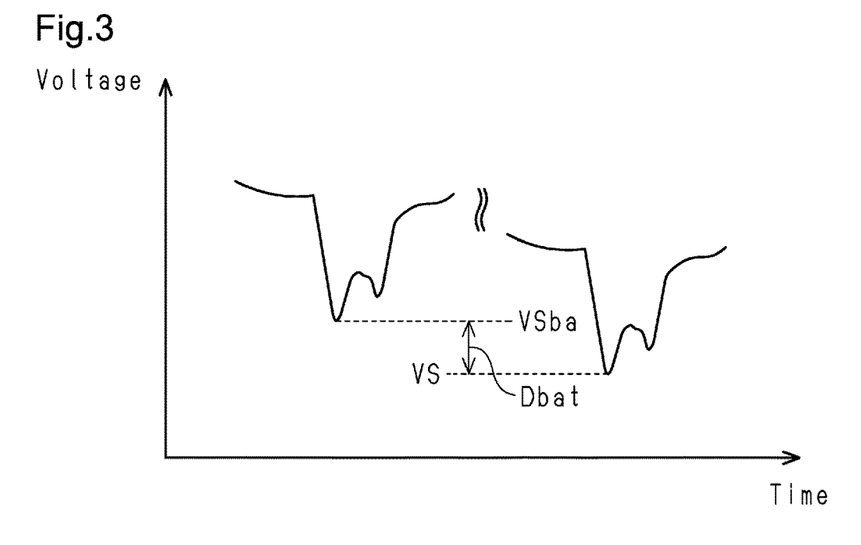
FIG. 3 is a diagram showing a battery degradation degree acquisition process in the first embodiment.

The controller 100 executes a battery degradation degree acquisition process that obtains a second degradation parameter Dbat. The second degradation parameter Dbat is used to quantify the degradation degree of the battery 75. The ROM 103 stores a battery degradation degree acquisition program in advance. Every time the internal combustion engine 10 is started, the CPU 101 executes the battery degradation degree acquisition program. The value of the second degradation parameter Dbat increases as the degradation degree increases.

Referring to FIG. 3, when the internal combustion engine 10 is started, the first motor generator 71 is driven by power from the battery 75. When a large current flows into the battery 75, the terminal-to-terminal voltage at the battery 75 drops significantly. In the present embodiment, the lowest terminal-to-terminal voltage at the battery 75 obtained when the first motor generator 71 is driven is referred to as the dropped peak voltage VS.

The memory device 104 stores a reference dropped peak voltage VSba. The reference dropped peak voltage VSba is defined in advance as the dropped peak voltage VS on the assumption that the battery 75 has not degraded. The CPU 101 obtains the dropped peak voltage VS when the internal combustion engine 10 is started in reality. The CPU 101 calculates, as the second degradation parameter Dbat, the amount in which the dropped peak voltage VS drops from the reference dropped peak voltage VSba. That is, as the difference between the reference dropped peak voltage VSba and the dropped peak voltage VS increases, the second degradation parameter Dbat increases.

Ambient Temperature Acquisition Process

The CPU 101 executes an ambient temperature acquisition process that obtains a predicted temperature FT outside the vehicle VC when the internal combustion engine 10 is started next. For example, the CPU 101 executes a date-and-time acquisition process that obtains, from the peripheral circuitry 102, a date and time DT at which the internal combustion engine 10 was started last. In addition, the memory device 104 stores a temperature map in which ambient temperature corresponds to season. In the temperature map, for example, temperatures respectively correspond to multiple periods into which one year (fixed period) is divided. For instance, one year is divided into four periods, namely, spring, summer, autumn, and winter.

Using the date and time DT and the temperature map obtained from the peripheral circuitry 102, the CPU 101 identifies a period that includes the date and time DT. The CPU 101 obtains the temperature corresponding to that period, as the predicted temperature FT outside the vehicle VC when the internal combustion engine 10 is started next.

Series of Processes that Calculate Oil Change Time for Lubricating Oil

Figure 4:
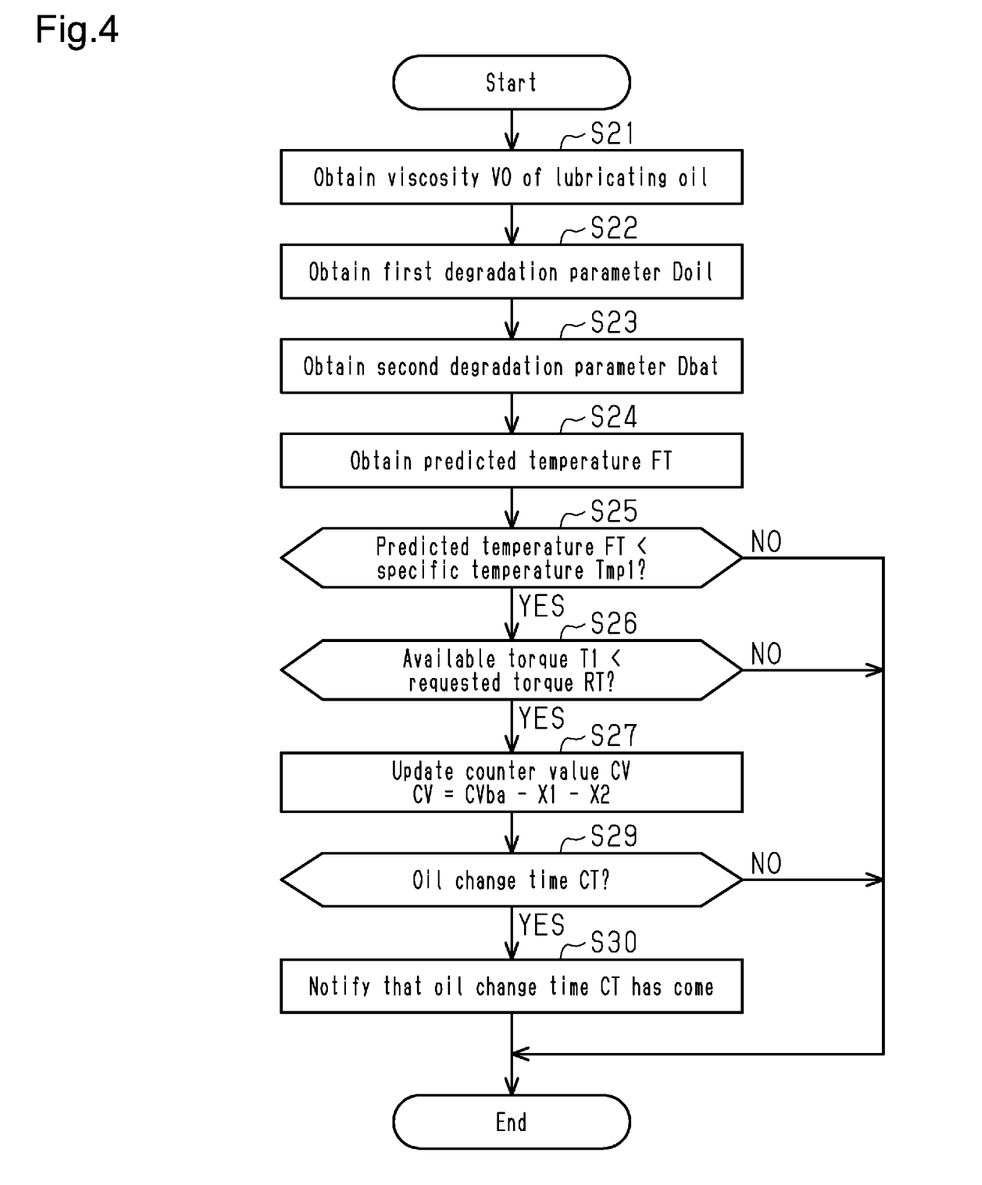
FIG. 4 is a flowchart showing a process that calculates the oil change time for a lubricating oil in the first embodiment.

A series of processes that calculate the oil change time for a lubricating oil will now be described. Every time the starting of the internal combustion engine 10 is completed, the CPU 101 once executes a process that calculates the oil change time for a lubricating oil by executing an oil change time calculation program, which is stored in the ROM 103.

As shown in FIG. 4, when the starting of the internal combustion engine 10 is completed, the CPU 101 executes step S21. In step S21, the CPU 101 obtains the viscosity VO of a lubricating oil by executing the viscosity acquisition process. Then, the CPU 101 advances the process to step S22.

In step S22, the CPU 101 obtains the first degradation parameter Doil that has been updated by the lubricating oil degradation degree acquisition process. Then, the CPU 101 advances the process to step S23.

In step S23, the CPU 101 obtains the second degradation parameter Dbat by executing the battery degradation degree acquisition process. Then, the CPU 101 advances the process to step S24.

In step S24, the CPU 101 obtains the predicted temperature FT, which is the temperature outside the vehicle VC, by executing the ambient temperature acquisition process. Then, the CPU 101 advances the process to step S25.

In step S25, the CPU 101 determines whether the predicted temperature FT is lower than a preset specific temperature Tmp1. The specific temperature Tmp1 is preset as a temperature at which the output voltage at the battery 75 decreases suddenly in a case where the output voltage at the battery 75 decreases as the temperature decreases. When the predicted temperature FT is lower than the specific temperature Tmp1 (S25: YES), the CPU 101 advances the process to step S26.

In step S26, the CPU 101 hypothesizes the time during which the vehicle VC has traveled a reference travel distance after the lubricating oil was changed, and determines whether an available torque T1 that can be output by the first motor generator 71 is insufficient relative to the requested torque RT. That is, the available torque T1 is a predicted output of the first motor generator 71 at a future point in time at which the changing of the lubricating oil is recommended. The requested torque RT is a predicted torque needed to start the internal combustion engine 10 at a future point in time at which the changing of the lubricating oil is recommended. The available torque T1 is defined through tests and simulations, as a variable obtained from the predicted temperature FT. More specifically, as the predicted temperature FT decreases, the available torque T1 is calculated to be smaller. The requested torque RT is a load amount obtained by adding a constant initial load amount L1, a load amount L2 corresponding to the internal resistance of the battery 75, and a load amount L3 corresponding to the viscosity of the lubricating oil. When the requested torque RT exceeds the available torque T1, the internal combustion engine 10 is potentially unable to be started by the first motor generator 71.

The initial load amount L1 is a fixed amount unaffected by the degradation of the lubricating oil and/or the degradation of the battery 75. The load amount L2 of the internal resistance of the battery 75 increases as the degradation degree of the battery 75 increases. The load amount L3 corresponding to the viscosity of the lubricating oil increases as the degradation degree of the lubricating oil (i.e., the first degradation parameter Doil) increases. Also, the load amount L3 corresponding to the viscosity of the lubricating oil increases as the viscosity VO of the lubricating oil increases.

More specifically, the CPU 101 uses the first degradation parameter Doil and the viscosity VO of the lubricating oil to calculate the load amount L3 corresponding to the viscosity of the lubricating oil. The CPU 101 calculates the load amount L3 corresponding to the viscosity of the lubricating oil by hypothesizing an amount in which the degradation degree of the lubricating oil is maximized. Further, the CPU 101 calculates the load amount L3 corresponding to the viscosity of the lubricating oil such that the load amount L3 increases as the viscosity VO of the lubricating oil increases.

Additionally, the CPU 101 uses the second degradation parameter Dbat to calculate the load amount L2 corresponding to the internal resistance of the battery 75. The CPU 101 calculates the load amount L2 corresponding to the internal resistance of the battery 75 to be larger as the second degradation parameter Dbat increases.

The CPU 101 determines whether the available torque T1 is insufficient relative to the requested torque RT. When the available torque T1 is insufficient relative to the requested torque RT (S26: YES), the CPU 101 advances the process to step S27.

In step S27, the CPU 101 executes an oil change time calculation process that calculates an oil change time CT for the lubricating oil. More specifically, the CPU 101 subtracts a counter value CV stored in the memory device 104 so as to update the counter value CV. When the lubricating oil is changed, the memory device 104 initializes the counter value CV to a preset reference counter value CVba. For example, the reference counter value CVba is set to 5000 km where the vehicle VC is capable of traveling in a favorable manner without changing the lubricating oil. That is, the counter value CV indicates, for example, the remaining drivable distance. Thus, the CPU 101 calculates, as the oil change time CT, the point in time at which the counter value CV becomes a preset threshold value. Even if the vehicle VC has traveled a distance corresponding to the threshold value, the threshold value is set to an estimated distance where the internal combustion engine 10 can be started next.

The CPU 101 subtracts a first correction amount X1 from the reference counter value CVba and further subtracts a second correction amount X2 so as to update the counter value CV. The CPU 101 calculates the value of the first correction amount X1 to be larger as the first degradation parameter Doil increases. Further, the CPU 101 calculates the second correction amount X2 using a correction map in which the second degradation parameter Dbat and the predicted temperature FT are inputs and the second correction amount X2 is output. In the correction map, the first correction amount X1 increases in correspondence with an increase in the second degradation parameter Dbat. In the correction map, the second correction amount X2 increases in correspondence with a decrease in the predicted temperature FT. In this manner, the first correction amount X1 increases as the first degradation parameter Doil increases (i.e., the degradation degree of a lubricating oil increases).

Accordingly, the counter value CV obtained by subtracting the first correction amount X1 and the second correction amount X2 from the reference counter value CVba is calculated to be smaller as the degradation degree of a lubricating oil increases. As the counter value CV decreases, the oil change time CT at which the counter value CV becomes zero becomes earlier. Then, the CPU 101 updates the counter value CV stored in the memory device 104. Subsequently, the CPU 101 advances the process to step S29.

When the predicted temperature FT is greater than or equal to the specific temperature Tmp1 (S25: NO) or when the available torque T1 is greater than or equal to the requested torque RT (S26: NO), the CPU 101 ends the series of processes.

In step S29, the CPU 101 executes an oil change time determination process that determines whether the oil change time CT has come. More specifically, the CPU 101 determines whether the counter value CV stored in the memory device 104 is a preset threshold value. More specifically, the CPU 101 determines whether the counter value CV indicating the remaining drivable distance is, for example, less than 100 km as a threshold value. The first correction amount X1 continues to increase unless the lubricating oil is changed. At a constant predicted temperature FT, the second correction amount X2 continues to increase unless the battery 75 is replaced. Accordingly, the counter value CV generally continues to decrease.

When the counter value CV is less than 100 km, the CPU 101 determines that the oil change time for the lubricating oil has come. In the same manner, when the counter value CV is negative, the CPU 101 determines that the oil change time CT for the lubricating oil has come. Thus, the time indicating the oil change time CT is calculated to be earlier when the counter value CV is calculated to be smaller. When determining that the oil change time for the lubricating oil has come (S29: YES), the CPU 101 advances the process to step S30.

In step S30, an output process is executed to output a notification signal indicating that the oil change time CT for the lubricating oil has come. For example, the CPU 101 outputs the notification signal to a display (not shown) of the vehicle VC so as to display a message indicating that the lubricating oil needs changing. Subsequently, the CPU 101 advances the process to step S30.

When completing the process of step S30 or when determining that the oil change time CT for the lubricating oil has not come (S29: NO), the CPU 101 ends the series of processes that calculate the current oil change time CT for the lubricating oil.

The operation of the first embodiment will now be described. In the following description, it is assumed that the viscosity VO of a lubricating oil is always constant.

Figure 5:
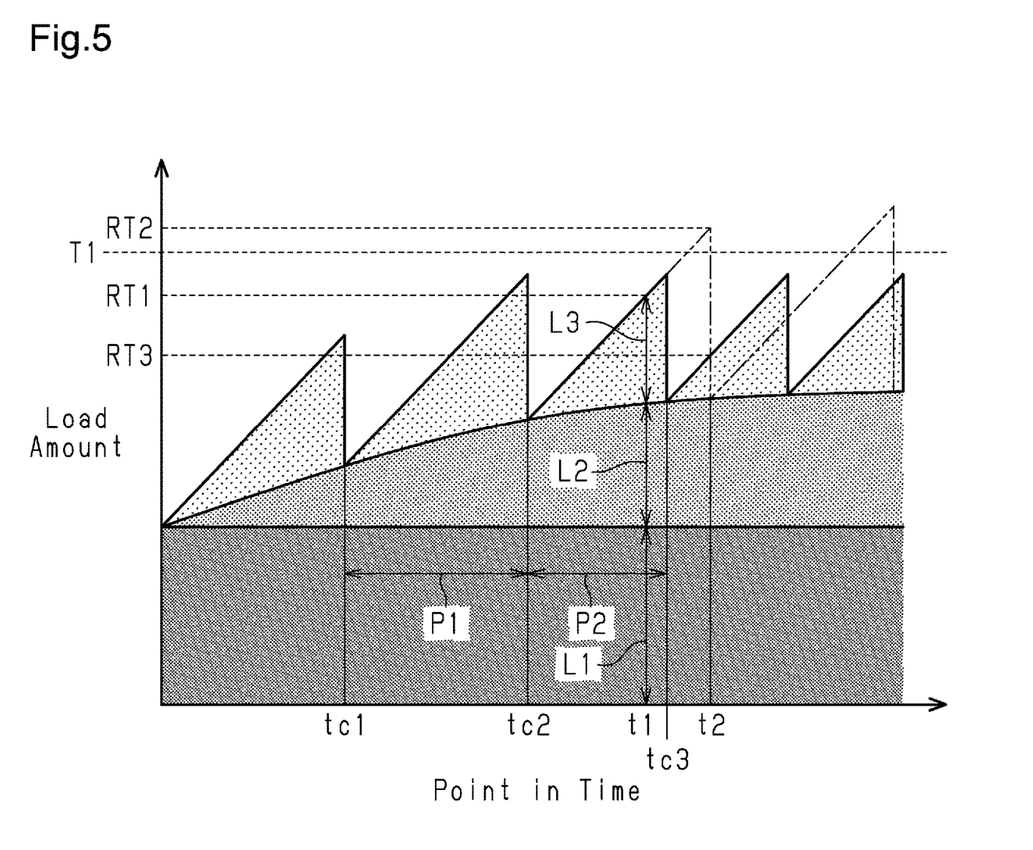
FIG. 5 is a graph showing changes in the requested torque in the first embodiment.

In the following description, as shown in FIG. 5, it is assumed that a first-time lubricating oil change is performed as a specific point in time tc1. Further, it is assumed that a second-time lubricating oil change is performed at a point in time tc2. The point in time tc2 is reached after a period P1 has elapsed since the point in time tc1. The period P1 corresponds to a period needed for a travel of 5000 km, which is the reference counter value CVba.

As shown in FIG. 5, for example, subsequent to the point in time tc2, at a point in time t1 before the travel of 5000 km (reference counter value CVba), when the internal combustion engine 10 is started, the requested torque RT1 is calculated as the total value of the initial load amount L1, the load amount L2 corresponding to the battery internal resistance, and the load amount L3 corresponding to the viscosity of a lubricating oil. At the point in time t1, the available torque T1 is sufficient relative to the requested torque RT1 and thus the internal combustion engine 10 can be started.

Hypothetically, a point in time t2 is where a period needed for the travel of a distance corresponding to the reference counter value CVba has elapsed since the point in time tc2. The load amount L3 corresponding to the viscosity of the lubricating oil at the point in time t2 is the same as the load amount L3 at the point in time tc2. In contrast, the battery 75 degrades to a larger extent at the point in time t2 than at the point in time tc2. Accordingly, the load amount L2 corresponding to the battery internal resistance at the point in time t2 is greater than the load amount L2 corresponding to the battery internal resistance at the point in time tc2. As a result, the available torque T1 is insufficient relative to a requested torque RT2. Thus, the internal combustion engine 10 is potentially unable to be started.

In the first embodiment, it is first determined at the point in time tc2 that the available torque T1 is insufficient relative to the requested torque RT2 that is calculated by hypothesizing the point in time t2 where the vehicle has traveled a reference travel distance since the lubricating oil was changed. Then, the counter value CV is updated by calculating the second correction amount X2 in correspondence with the second degradation parameter Dbat, which is used to quantify the degradation of the battery 75, and subtracting the second correction amount X2 from the reference counter value CVba. Accordingly, a point in time tc3 is calculated as the oil change time CT. The point in time tc3 is reached after a period P2 has elapsed since the point in time tc2. Period P2 is shorter than the period needed for the travel distance represented by the reference counter value CVba.

At the point in time tc3, when the lubricating oil is changed, the load amount L3 corresponding to the viscosity of the lubricating oil becomes zero. Thus, the available torque T1 is sufficient relative to the requested torque RT3 even if the point in time t2 is reached subsequent to the point in time tc3. This allows the internal combustion engine 10 to be started.

The advantages of the first embodiment will now be described.

(1-1) In the first embodiment, the load amount that can be output by the first motor generator 71 decreases as the second degradation parameter Dbat (i.e., the degradation degree of the battery 75) increases. Thus, at a large degradation degree of the battery 75, the internal combustion engine 10 is potentially unable to be started by the first motor generator 71 even if the degradation degree of the lubricating oil is not large. In the first embodiment, the oil change time CT is calculated so as to become earlier as the degradation degree of the battery 75 increases. Accordingly, even if the available torque T1 of the first motor generator 71 is decreased by an increase in the degradation degree of the battery 75, situations in which the internal combustion engine 10 cannot be started are avoided by prompting the changing of the lubricating oil.

(1-2) In the first embodiment, the oil change time calculation process is executed when the predicted temperature FT is smaller than the specific temperature Tmp1, that is, when the influence of the battery degradation is large. This prevents the oil change time calculation process from being executed unnecessarily when the degradation of the battery 75 demonstrates a relatively small influence and the internal combustion engine 10 can be started.

(1-3) In the first embodiment, the ambient temperature acquisition process obtains the predicted temperature FT from the date and time DT. Thus, even if the temperature outside the vehicle VC is not directly obtained, the predicted temperature FT can be obtained from the temperature information that includes the date and time DT.

(1-4) In the first embodiment, the second correction amount X2 is calculated to be larger as the predicted temperature FT decreases. Thus, in the first embodiment, the oil change time CT is corrected so as to become earlier as the predicted temperature FT decreases. This allows the oil change time CT to be adjusted in correspondence with the predicted temperature FT.

(1-5) In the first embodiment, the point in time at which the vehicle has traveled the reference travel distance since the lubricating oil was changed is hypothesized. On this hypothesis, when the available torque T1 is insufficient relative to the requested torque RT, the oil change time calculation process in step S27 is executed. When the available torque T1 is sufficient relative to the requested torque RT, the series of processes are ended without updating the counter value CV. Thus, in a case where the available torque T1 is sufficient relative to the requested torque RT at the point in time at which the vehicle VC has traveled the reference travel distance since the lubricating oil was changed, the updating of the counter value CV and the calculation of the oil change time CT based on the counter value CV are not performed. This reduces the processing load on the CPU 101 when the internal combustion engine 10 can be started.

Second Embodiment

Figure 6:
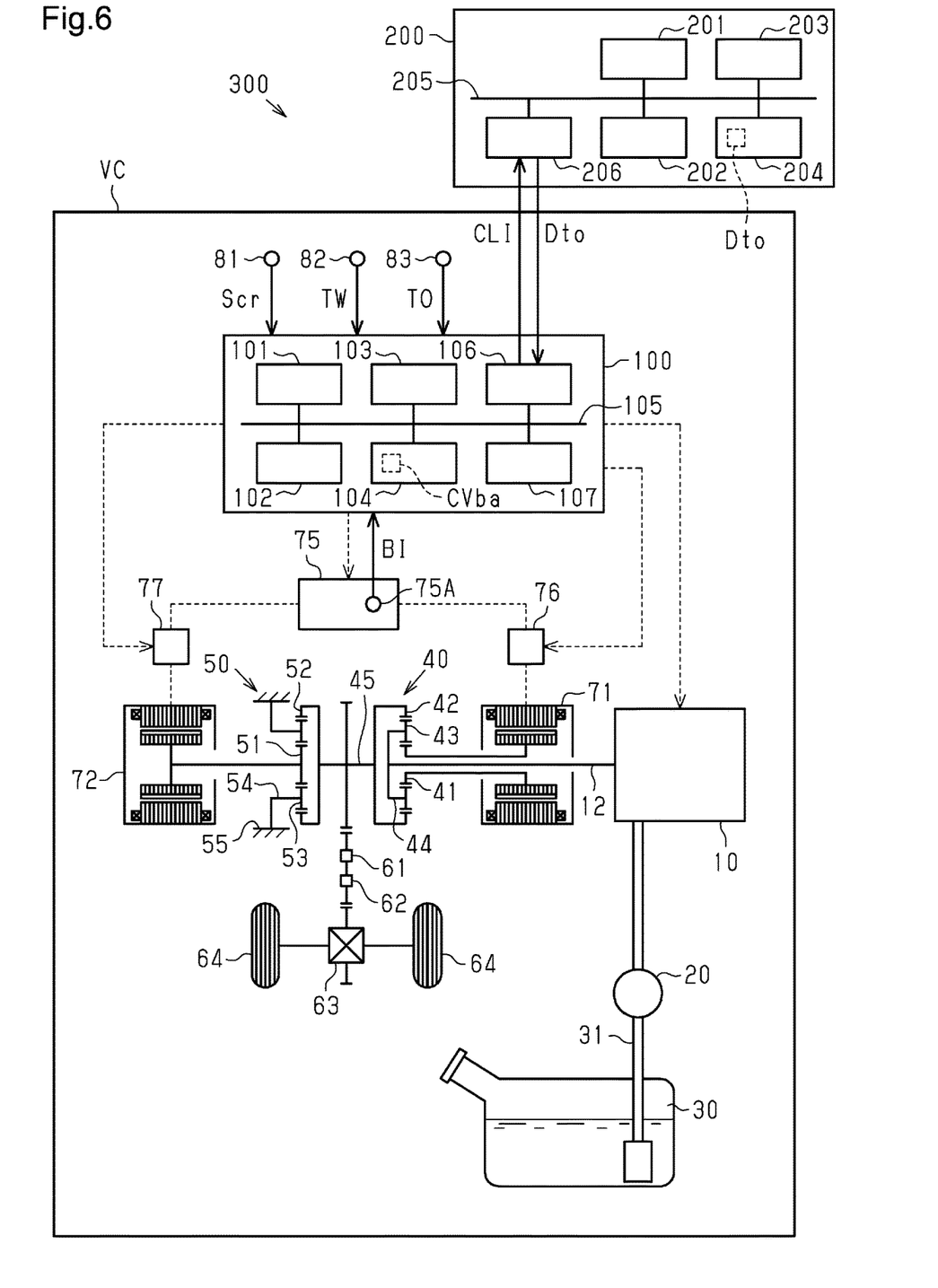
FIG. 6 is a diagram schematically showing the configuration of the vehicle according to a second embodiment.

The controller 100 for the vehicle VC according to a second embodiment will now be described. Those components that are the same as the corresponding components of the first embodiment will be described simply or will not be described. In the second embodiment, the vehicle VC in which the controller 100 of the present disclosure is employed is part of a vehicle system 300. The second embodiment mainly differs from the first embodiment in the ambient temperature acquisition process. The differences will now be mainly described.

Schematic Configuration of Vehicle System

As shown in FIG. 6, the vehicle system 300 includes the vehicle VC and an external server 200. The controller 100 for the vehicle VC includes a communication device 106 and a GPS device 107. The bus 105 connects the communication device 106 and GPS device 107 to the CPU 101, peripheral circuitry 102, ROM 103, and memory device 104 such that they are communicable with each other.

The external server 200 includes a CPU 201, peripheral circuitry 202, a ROM 203, a memory device 204, a bus 205, and a communication device 206. The bus 205 connects the CPU 201, the peripheral circuitry 202, the ROM 203, the memory device 204, and the communication device 206 such that they are communicable with each other. The peripheral circuitry 202 includes a circuit that generates a clock signal regulating internal operations, a power supply circuit, and a reset circuit. The ROM 203 stores, in advance, various programs with which the CPU 201 executes various types of control.

Ambient Temperature Acquisition Process

The CPU 201 of the external server 200 executes the various programs stored in the ROM 203 so as to predict future temperatures in different regions. The CPU 201 stores, in the memory device 204, changes in the temperatures in the regions over a fixed period in the future. The changes are stored as ambient temperature data Dto. The category of each region includes, for example, a state, a province, a county, a city, a town, and a village. The fixed period refers to, for example, a few hours or a few days.

When executing the ambient temperature acquisition process, the CPU 101 of the vehicle VC sends, via the communication device 106 to the external server 200, a signal requesting the ambient temperature data Dto with current position information CL1 of the vehicle VC received by the GPS device 107. Subsequently, the CPU 101 of the vehicle VC waits for the response from the external server 200.

After receiving the signal from the vehicle VC, the CPU 201 of the external server 200 uses the current position information CL1 of the vehicle VC to identify the region where the vehicle VC is located. The CPU 201 sends, via the communication device 206 to the CPU 101, the ambient temperature data Dto of the region where the vehicle VC is located.

The CPU 101 of the vehicle VC receives the ambient temperature data Dto through the communication device 106. Specifically, the CPU 101 of the vehicle VC executes a data acquisition process that obtains, through the communication device 106, the ambient temperature data Dto related to a future temperature outside the vehicle VC. After receiving the ambient temperature data Dto, the CPU 101 of the vehicle VC uses the obtained ambient temperature data Dto to estimate the predicted temperature FT and thus obtain the predicted temperature FT. For example, the CPU 101 obtains the lowest ambient temperature of the ambient temperature data Dto as the predicted temperature FT.

The advantages of the second embodiment will now be described. In addition to the advantages (1-1), (1-2), (1-4), and (1-5) of the first embodiment, the second embodiment provides the following advantages.

(2-1) In the second embodiment, the ambient temperature acquisition process obtains the predicted temperature FT from the ambient temperature data Dto, which is obtained through the communication device 106. This allows, for example, the predicted temperature FT to be obtained without using the ambient temperature sensor 84 in the vehicle VC.

(2-2) The external server 200, which predicts future temperatures in different regions, is not included in the vehicle VC. Further, the external server 200 can be shared by multiple vehicles VC. Accordingly, a large-scale external server 200 can be employed in order to increase the accuracy of predicting temperatures.

MODIFICATIONS

The above-described embodiments may be modified as follows. The above-described embodiments and the following modifications can be combined as long as the combined modifications remain technically consistent with each other.

In each of the above-described embodiments, the ambient temperature acquisition process is not limited to the example of each of the above-described embodiments. For example, in the first embodiment, the predicted temperature FT may be obtained by estimating the predicted temperature FT from changes in ambient temperatures over a fixed period obtained from the ambient temperature sensor 84 of the vehicle. For example, the average value or the lowest value of ambient temperatures for a fixed period in the past can be estimated as the predicted temperature FT. In such a case, since the predicted temperature FT is obtained from the ambient temperatures obtained by the ambient temperature sensor 84, there is no need to, for example, communicate with a device outside the vehicle.

In each of the above-described embodiments, the ambient temperature acquisition process may obtain ambient temperatures using multiple methods so as to obtain the most suitable one of the values as the predicted temperature FT. For example, an ambient temperature acquisition process using the ambient temperature sensor 84 and an ambient temperature acquisition process based on the date and time DT simply need to be executed. In this case, when one of the values is calculated to be smaller than the other one of the values, the predicted temperature FT simply needs to be obtained as the smaller one of the values.

In each of the above-described embodiments, the predicted temperature FT may be obtained using an intake air temperature sensor that detects the temperature of intake air, instead of the ambient temperature sensor 84.

In each of the above-described embodiments, the predicted temperature FT is obtained as a temperature outside the vehicle when the internal combustion engine 10 is started next. A next start estimation process may be executed to estimate a next start time of the internal combustion engine 10. The next start estimation process may cause for example, a user to input a date and time at which the internal combustion engine 10 will be started next, as the next start time. Further, if the start time of the internal combustion engine 10 in the past has regularity, the next start time may be estimated in accordance with the regularity. Executing the next start estimation process in this manner increases the likelihood of improving the accuracy of the predicted temperature FT.

In the first embodiment, one year is divided into four periods, namely, spring, summer, autumn, and winter in the temperature map such that a temperature corresponds to each period. Instead, for example, one year may be divided into twelve periods on a monthly basis such that a temperature corresponds to each period. Additionally, in the first embodiment, one year is treated as a specific fixed period in the temperature map. Instead, one day may be treated as a specific period such that one day is divided into three periods, namely, morning, noon, and evening.

In each of the above-described embodiments, whether the counter value CV is calculated in correspondence with the second correction amount X2 is determined depending on whether the predicted temperature FT is lower than the preset specific temperature Tmp1. The process of step S25 is not limited to this example. For example, in the second embodiment, to obtain changes in ambient temperatures over a fixed period in the past, an integral value obtained by integrating the ambient temperatures over the fixed period in the past with respect to time may be determined in comparison with a preset specific value. In this case, the predicted temperature FT is predicted to be sufficiently large when the integral value is greater than or equal to a specific value, and the predicted temperature FT is predicted to be sufficiently small when the integral value is less than the specific value.

In each of the above-described embodiments, the process of step S26 may be omitted. Alternatively, the process of step S26 may be changed so as to determine whether the degradation degree of the battery 75 is greater than a specific value. For example, the process is advanced to step S27 when the second degradation parameter Dbat is greater than a specific value, and the series of processes may be ended when the second degradation parameter Dbat is less than or equal to the specific value. In this case, the specific value simply needs to be defined as, for example, a value at which the requested torque RT is equal to the available torque T1 when the load amount L3 corresponding to the viscosity of a lubricating oil is an amount obtained through a travel of the reference travel distance (e.g., 5000 km).

In each of the above-described embodiments, the viscosity acquisition process is not limited to the example of each of the above-described embodiments. For example, when the lubricating oil is changed, a preset viscosity VO may be input in correspondence with the type of the lubricating oil so that the viscosity VO is stored in the memory device 104. Alternatively, for example, the viscosity acquisition process may be omitted. In the above-described embodiments, the viscosity VO of a lubricating oil is obtained using the viscosity acquisition map. Instead, the viscosity VO of a lubricating oil may be obtained using a viscosity predication expression that includes the oil temperature TO as an input and the viscosity VO as an output.

In each of the above-described embodiments, the lubricating oil degradation degree acquisition process is not limited to the example of each of the above-described embodiments. For example, as long as the amounts of impurities in a lubricating oil is measurable, the first degradation parameter Doil, which indicates the degradation degree of a lubricating oil, may be calculated in correspondence with the amounts of impurities. Alternatively, the first degradation parameter Doil may be calculated in correspondence with the travel distance of the vehicle VC.

As another option, the first degradation parameter Doil may be calculated in correspondence with a fuel consumption amount consumed in a single combustion or a fuel consumption amount consumed per unit of time. More specifically, a fuel consumption amount detection sensor that detects a fuel amount consumed in a single combustion may be used to calculate the first degradation parameter Doil to be larger as the fuel consumption amount that is consumed in a single combustion and detected using the fuel consumption amount detection sensor increases. Instead, the fuel consumption amount consumed per unit of time may be calculated from the fuel consumption amount that is consumed in a single combustion and detected using the fuel consumption amount detection sensor. As the fuel consumption amount consumed per unit of time increases, the first degradation parameter Doil may be calculated to become larger. The fuel consumption amount consumed in a single combustion may be calculated from a fuel consumption amount injected in a single combustion, instead of using the fuel consumption amount detection sensor.

In each of the above-described embodiments, the battery degradation degree acquisition process is not limited to the example of each of the above-described embodiments. For example, the degradation degree of the battery 75 may be estimated from the time during which the battery 75 is used (more specifically, the total charging time and the total discharging time) or may be estimated from a decrease ratio of the charge amount to the discharge amount. Instead, for example, the degradation degree of the battery 75 may be calculated and obtained in correspondence with the travel distance of the vehicle VC.

In each of the above-described embodiments, the battery information BI including the input current, output current, output voltage, and temperature of the battery 75 may be estimated from, for example, a cranking speed obtained when the internal combustion engine 10 is started, the temperature of intake air, or the coolant temperature TW. In the battery degradation degree acquisition process, the battery information BI estimated in this manner may be used to estimate the degradation amount of the battery 75.

In each of the above-described embodiments, in a case where the series of processes shown in FIG. 4 are executed at the point in time at which the starting of the internal combustion engine 10 is completed, the processes do not have to be executed every time. For example, the series of processes shown in FIG. 4 may be executed every time a specific period elapses, every time the vehicle VC travels a specific distance, or every time the lubricating oil is changed.

In each of the above-described embodiments, the oil change time calculation process for a lubricating oil may be executed regardless of the predicted temperature FT.

In each of the above-described embodiments, the oil change time CT may be calculated regardless of whether the predicted temperature FT is high or low. When the oil change time calculation process for a lubricating oil is executed regardless of the predicted temperature FT and the oil change time calculation process is executed regardless of whether the predicted temperature FT is high or low, the ambient temperature acquisition process may be omitted.

In each of the above-described embodiments, the point in time at which the counter value CV becomes a threshold value is calculated as the oil change time CT. Instead, for example, the oil change time CT may be calculated as the remaining travel distance until the lubricating oil needs changing. In this case, the process that calculates the counter value CV serves as the process that calculates the oil change time CT. Additionally, for example, a map may be used in which the first degradation parameter Doil and the second degradation parameter Dbat are inputs and the oil change time CT is output as the remaining time. In this map, the remaining time is calculated to be smaller as the first degradation parameter Doil increases and the second degradation parameter Dbat increases. In such a manner, the oil change time CT simply needs to be calculated at least such that the oil change time CT becomes earlier as the degradation degree of the battery 75 increases.

In each of the above-described embodiments, the output process is not limited to the example of each of the above-described embodiments. The output process simply needs to output a communication signal used to notify that the oil change time CT has come. For example, the communication signal may be output by voice or may be output via the communication device 106 to a mobile terminal carried by the user. Instead of or in addition to displaying a message, the counter value CV may be displayed as the remaining travel distance until the lubricating oil should be changed.

In each of the above-described embodiments, an additional process may be executed to display a message indicating that the battery 75 needs replacing. For example, when the lubricating oil is changed at a dealership, the display indicating that the lubricating oil should be changed is cancelled. For the new lubricating oil, it is determined whether the available torque T1 is insufficient relative to the requested torque RT. When the available torque T1 is determined as being insufficient relative to the requested torque RT in the new lubricating oil, a message indicating that the battery 75 needs replacing is displayed on the display.

In each of the above-described embodiments, the vehicle VC in which the controller 100 is employed is a hybrid electric vehicle. Instead, the vehicle VC in which the controller 100 is employed simply needs to include at least the internal combustion engine 10, a motor that starts the internal combustion engine 10, and a battery that supplies power to the motor. For example, the motor may be a starter motor that starts the internal combustion engine 10, and the battery may be an auxiliary battery that supplies power to the starter motor.

In each of the above-described embodiments, the controller 100 is not limited to a device that includes the CPU 101 and the ROM 103 and executes software processing. For example, at least part of the processes executed by the software in the above-described embodiments may be executed by hardware circuits dedicated to executing these processes (such as ASIC). That is, the controller 100 may be modified as long as it has any one of the following configurations (a) to (c): (a) a configuration including a processor that executes all of the above-described processes according to programs and a program storage device such as a ROM that stores the programs; (b) a configuration including a processor and a program storage device that execute part of the above-described processes according to the programs and a dedicated hardware circuit that executes the remaining processes; and (c) a configuration including a dedicated hardware circuit that executes all of the above-described processes. A plurality of software execution devices each including a processor and a program storage device and a plurality of dedicated hardware circuits may be provided.

Various changes in form and details may be made to the examples above without departing from the spirit and scope of the claims and their equivalents. The examples are for the sake of description only, and not for purposes of limitation. Descriptions of features in each example are to be considered as being applicable to similar features or aspects in other examples. Suitable results may be achieved if sequences are performed in a different order, and/or if components in a described system, architecture, device, or circuit are combined differently, and/or replaced or supplemented by other components or their equivalents. The scope of the disclosure is not defined by the detailed description, but by the claims and their equivalents. All variations within the scope of the claims and their equivalents are included in the disclosure.

What is claimed is:

1. A controller for a vehicle, the vehicle including an internal combustion engine, a motor that starts the internal combustion engine, and a battery that supplies power to the motor, wherein the controller is configured to execute:

a lubricating oil degradation degree acquisition process that calculates a degradation degree of a lubricating oil that lubricates the internal combustion engine;

a battery degradation degree acquisition process that calculates a degradation degree of the battery;

an oil change time calculation process that calculates an oil change time for the lubricating oil from the degradation degree of the lubricating oil and the degradation degree of the battery, and the oil change time calculation process includes calculating the oil change time so as to become earlier as the degradation degree of the battery increases; and an output process that outputs to a display a notification based on the oil chance time.

2. The controller according to claim 1, wherein
the controller is configured to execute an ambient temperature acquisition process that obtains a predicted temperature outside the vehicle when the internal combustion engine is started next, and
the controller executes the oil change time calculation process when the predicted temperature is lower than a preset specific temperature.

3. The controller according to claim 2, wherein
the vehicle includes an ambient temperature sensor that measures a temperature outside the vehicle, and
the ambient temperature acquisition process includes obtaining the predicted temperature by estimating the predicted temperature from changes in an ambient temperature over a fixed period obtained from the ambient temperature sensor.

4. The controller according to claim 2, wherein
the vehicle includes a communication device capable of communicating with a device outside the vehicle,
the controller is configured to execute a data acquisition process that obtains, through the communication device, ambient temperature data related to a future temperature outside the vehicle, and
the ambient temperature acquisition process includes obtaining the predicted temperature by estimating the predicted temperature from the ambient temperature data obtained by the data acquisition process.

5. The controller according to claim 2, further comprising a memory device that stores multiple periods into which a specific fixed period is divided and stores a temperature corresponding to each of the multiple periods, wherein
the controller is configured to execute a date-and-time acquisition process that obtains a date and time when the internal combustion engine is started, and
the ambient temperature acquisition process includes obtaining the predicted temperature by estimating, as the predicted temperature, a temperature corresponding to one of the periods that includes the date and time.

6. The controller according to claim 2, wherein
the controller is configured to execute a next start estimation process that estimates a next start time at which the internal combustion engine is started next, and
the ambient temperature acquisition process includes obtaining, as the predicted temperature, a temperature outside the vehicle at the next start time obtained by the next start estimation process.

7. The controller according to claim 1, wherein
the controller is configured to execute an ambient temperature acquisition process that obtains a predicted temperature outside the vehicle when the internal combustion engine is started next, and
the oil change time calculation process includes calculating the oil change time so as to become earlier as the predicted temperature decreases as compared with when the predicted temperature increases.

8. A method for controlling a vehicle, the vehicle including an internal combustion engine, a motor that starts the internal combustion engine, and a battery that supplies power to the motor, the method comprising:
- calculating a degradation degree of a lubricating oil that lubricates the internal combustion engine;
- calculating a degradation degree of the battery;
- calculating an oil change time for the lubricating oil from the degradation degree of the lubricating oil and the degradation degree of the battery, wherein the calculating the oil change time includes calculating the oil change time so as to become earlier as the degradation degree of the battery increases; and
- outputting to a display a notification based on the oil change time.

* * * * *